United States Patent
Fein et al.

(10) Patent No.: US 10,136,648 B1
(45) Date of Patent: Nov. 27, 2018

(54) FISH ATTRACTION COMPOSITION

(71) Applicants: Peter Fein, Waccabuc, NY (US); Peter Wachtel, Scotch Plains, NJ (US)

(72) Inventors: Peter Fein, Waccabuc, NY (US); Peter Wachtel, Scotch Plains, NJ (US)

( * ) Notice: Subject to any disclaimer, the term of this patent is extended or adjusted under 35 U.S.C. 154(b) by 42 days.

(21) Appl. No.: 15/209,002

(22) Filed: Jul. 13, 2016

(51) Int. Cl.
*A01N 63/00* (2006.01)
*A01N 25/34* (2006.01)
*A01K 85/01* (2006.01)

(52) U.S. Cl.
CPC ............. *A01N 63/00* (2013.01); *A01K 85/01* (2013.01); *A01N 25/34* (2013.01)

(58) Field of Classification Search
CPC ......... A01N 61/00; A01N 25/34; A01K 85/00
See application file for complete search history.

(56) References Cited

U.S. PATENT DOCUMENTS

| | | | | |
|---|---|---|---|---|
| 3,822,211 A * | 7/1974 | Morton | ................ | A01K 97/045 424/84 |
| 4,826,691 A * | 5/1989 | Prochnow | .............. | A01K 85/01 426/1 |
| 4,875,305 A | 10/1989 | Bridges | | |
| 4,887,376 A | 12/1989 | Sibley | | |
| 4,901,466 A * | 2/1990 | Davis | ..................... | A01K 85/01 43/4 |
| 4,927,643 A | 5/1990 | D'Orazio et al. | | |
| 4,962,609 A | 10/1990 | Walker | | |
| 5,089,277 A * | 2/1992 | Prochnow | ............ | A01K 97/045 426/1 |
| 5,097,616 A | 3/1992 | Johnston, Jr. | | |
| 5,269,087 A | 12/1993 | Johnston | | |
| 5,374,600 A * | 12/1994 | Hozumi | ................ | A01K 97/045 502/402 |
| 5,827,551 A * | 10/1998 | Prochnow | .............. | A01K 85/01 426/1 |
| 6,079,146 A | 6/2000 | Larsen | | |
| 6,143,333 A * | 11/2000 | Lanter | ................... | A01K 97/045 424/84 |
| 6,298,595 B1 * | 10/2001 | Friedlob | ................ | A01K 97/02 43/42.06 |
| 6,632,786 B1 | 10/2003 | Wyatt | | |
| 6,748,900 B2 * | 6/2004 | Harris, Jr. | .............. | A01K 79/00 119/231 |
| 6,827,930 B2 * | 12/2004 | Cobb | ..................... | A01K 85/01 424/405 |
| 6,843,986 B1 * | 1/2005 | McMaster | ............ | A01K 97/045 424/84 |
| 7,805,878 B2 | 10/2010 | Thomson | | |
| 8,919,662 B2 * | 12/2014 | Sherwood | ........... | A01M 1/2055 239/36 |
| 8,931,204 B1 | 1/2015 | Thomson | | |
| 2002/0188057 A1 * | 12/2002 | Chen | ..................... | A01K 85/00 524/575 |
| 2016/0345566 A1 * | 12/2016 | Niederhauser | ......... | A01K 85/00 |

* cited by examiner

*Primary Examiner* — Christopher P Ellis

(57) ABSTRACT

A composition is provided that will combine with natural proteins into a creamy, sticky substance that will slowly degrade when submersed in water within a temperature range of 45-85 ⁰F over a period of 15 to 30 minutes or longer or approximately 15-30 casts by the fisherman before replenishment is needed. The sticky aspect is measured by its ability to adhere to soft rubber, hard plastic, or metal lures. The timing of release is measured by release on first cast through the last cast, preferably gradually degrading by being a homogeneous form. The amount of release is measured by the maximum amount by % in weight that the formula will accept within desired results.

16 Claims, No Drawings

FISH ATTRACTION COMPOSITION

FIELD OF THE INVENTION

The field of the invention is fishing in particular a method and composition to stimulate fish to take a lure or hook.

BACKGROUND OF THE INVENTION

Fishing is a popular pasttime worldwide. Many different attractants for inducing fish to take or bite a lure have been proposed. Lures of a myriad of shapes have been proposed. See for example U.S. Pat. No. 4,962,609 (Walker); U.S. Pat. No. 8,931,204 (Thomson). Colored or scented lures have been proposed. Such devices are often cumbersome or of limited effectiveness. Scent applied to lures often quickly dissapates providing limited fish attraction. It is desired that a fish attractant permeate from the lure to attract the fish to the lure and mimic the scent of natural bait for an extended period of time.

One area of particular interest is that of chemical fish attractants and the formulations for delivering them to the target fish. Fish attractants should be water soluble to be effective. Unfortunately, water soluble attractants of the prior art are quickly removed from a lure when applied as a surface coating. Various formulations have been disclosed for releasing the water soluble fish attractants. See U.S. Pat. No. 5,827,551 (Prochnow). There is still a need for a fish attractant that is slowly water soluble but permeates into the water from the lure at a slow rate.

SUMMARY OF THE INVENTION

According to the invention, a fish attractant composition having a natural scent derived from food sources that fish are accustomed to eating in fresh and salt water environments is provided. Desirably the composition will release a potent scent when immersed in water within a defined temperature range and specific time period typical in most fishing scenarios.

The attractant composition is water soluble by design to enhance the attraction functions of any artificial bait or lure, whether metal, soft or hard plastic, and with a primary function to stimulate predatory fish to chase and bite a lure with the attractant in greater frequency than without. The attractant should remain on the lure for ten minutes or longer desirably 15 to 30 minutes while diffusing into the surrounding water to attract the fish.

Artificial baits or lures typically stimulate the visual sensory receptors of predator fish, by shape, by movement, by color, by reflection and some with sound (auditory) attributes. Some lures claim of being scent attracting (olfactory) and bite stimulating (gustatory) integrated into the lure composition.

Lures that boast of scent trailing attributes will have a limited ability if the composition binding the scent to the lure, does not degrade while immersed in water, leaving the extent of attractant available to be released to the limited amount of scent located on surface areas only. As water soluble scents on their own will disperse rapidly when immersed in water, a binder is needed that will release within a temperature range and will sustain over a calculated time period recognizing a fisherman's normal cycle.

According to the invention, a composition is provided that will combine with natural proteins into a creamy, sticky substance that will slowly degrade when submersed in water within a temperature range of 45-85° F. over a period of 15 to 30 minutes or longer or approximately 15-30 casts by the fisherman before replenishment is needed. The sticky aspect is measured by its ability to adhere to soft rubber, hard plastic, or metal lures. The timing of release is measured by release on first cast through the last cast, preferably gradually degrading by being a homogeneous form. The amount of release is measured by the maximum amount by % in weight that the formula will accept within desired results.

According to the invention, a fish attractant made of one or more polyethylene glycol polymers having a mw of about 300 to 4000 in an amount of 19% to 53% by weight of the fish attractant is provided. A polyethylene wax having a mw of about 220 to 560 in an amount of about 7% to 22% by weight of the fish attractant and petroleum jelly in an amount of about 5% to about 20% by weight of the fish attractant are mixed with the polyethylene glycol polymers while heating to form a flowable mixture. A scent attractant in an amount of about 16% to 60% of by weight of the fish attractant is mixed therewith. The resulting mixture is poured into a container desirably a tube to cool and solidify to a waxy, creamy, sticky substance than can be easily applied to a fishing lure. The fish attractant will slowly disperse into the water when submersed in water within a temperature range of 45-85° F. over a period of 15 to 30 minutes or approximately 15-30 casts.

In another aspect of the invention, a fish attractant formed from two polyethylene glycol polymers, a polyethylene wax, and petroleum jelly to form a binder for a scent is provided. The first polyethylene glycol polymer has a mw of about 300 to 960 and is present in an amount of about 9% to 22% by weight of the fish attractant. The second polyethylene glycol polymer has a mw of about 1200 to 3600 and is present in an amount of about 18% to 31% by weight of the fish attractant. The polyethylene glycol polymers are mixed together with a polyethylene wax having a mw of about 220 to 560 in an amount of about 5%-23% by weight of the fish attractant and petroleum jelly in an amount of about 10%-25% by weight of the fish attractant. The composition is heated until the components form a flowable mixture. A scent in an amount of about 15% to 60% of the fish attractant is added to the flowable mixture under mixing. The mixture is poured into a container desirably a tube to cool and solidify to a waxy, creamy, sticky substance than can be easily applied to a fishing lure. The fish attractant will slowly disperse into the water when submersed in water within a temperature range of 45-85° F. over a period of 15 to 30 minutes or approximately 15-30 casts. The resulting fish attractant reflects UV light which is the primary light under water and results in an increased visibility of any coated lure to fish.

The preferred embodiment of the present invention is illustrated in the examples. However, it should be expressly understood that the present invention should not be limited solely to the illustrative embodiment.

DETAILED DESCRIPTION OF THE INVENTION

According to the invention, a fish attractant containing scent laden proteins that is a waxy, creamy, sticky substance that will slowly degrade when submersed in water within a temperature range of 45-85 ⊐F over a period of 15 to 30 minutes or approximately 15-30 casts by the fisherman before replenishment is provided. The sticky aspect is measured by its ability to adhere to soft rubber, hard plastic, metal lures or artificial baits. The timing of release is measured by an immediate release on first cast consistently through the last cast, preferably evenly degrading by being a homogeneous form. The amount of release is measured by the maximum amount by % in weight that the formula will accept within desired results.

According to the invention, a fish attractant made of one or more polyethylene glycol polymers having a mw of about 300 to 8000 in an amount of 19% to 49% by weight of the fish attractant is provided. A polyethylene wax having a mw of about 300 to 600 in an amount of about 5% to 20% by weight of the fish attractant and petroleum jelly in an amount of about 5% about 20% by weight of the fish attractant are mixed with the polyethylene glycol polymers while heating to form a flowable mixture. This flowable mixture acts as binder for a scent. A scent in an amount of about 20% to 60% of by weight of the fish attractant is mixed with the binder. The scent is desirably a natural or artificial scent, preferable a natural scent derived from a natural bait consumed by a fish, that the fisherman is targeting. preferably the scent is a gel for example a nightcrawler gel scent provide by ProCure, Salem, Or. Optionally the scent includes a UV reflective additive. Optionally the scent has salt and/or sugar in a range of 3 to 6% of formula as a water soluble dispersing agent. The resulting mixture is poured into a container desirably a tube to cool and solidify to a waxy, creamy, sticky substance than can be easily applied to a fishing lure. The fish attractant will slowly disperse into the water when submersed in water within a temperature range of 45-85° F. over a period of 15 to 30 minutes or approximately 15-30 casts.

In another aspect of the invention, a fish attractant formed from two polyethylene glycol polymers, a polyethylene wax, and petroleum jelly. The first polyethylene glycol polymer has a mw of about 300 to 1000 desirably a molecular weight of 520 to 630 preferably having a molecular weight of about 600 and is present in an amount of about 10% to 20% by weight preferably about 12.5% of the fish attractant. The second polyethylene glycol polymer has a mw of about 3000 to 5000 desirably 4300 to 4900 preferably about 4600 and is present in an amount of about 20% to 30% preferably 15% by weight of the fish attractant. The polyethylene glycol polymers are mixed together with a polyethylene wax having a mw of about 400 to 600 preferably about 500 in an amount of about 5%-15% preferably about 10% by weight of the fish attractant and petroleum jelly in an amount of about 10%-20% preferably about 12.5% by weight of the fish attractant. The composition is heated until the components form a flowable mixture desirably to a temperature of 140° F. to 200° F. preferably to about 170° F. A scent in an amount of about 40% to 60% of the fish attractant is added to the flowable mixture under mixing preferably at a temperature of 140° F. to 200° F. preferably at about 150° F. The scent is desirably a natural or artificial scent preferable a natural scent derived from a natural bait consumed by a fish, that the fisherman is targeting or optionally a fish scent. The mixture is poured into a container desirably a tube to cool desirably at room temperature and solidify to a waxy, creamy, sticky substance than can be easily applied to a fishing lure. Optionally salt, sugar or mixtures thereof can be added in amount of 3-6% as dispersing agents. The fish attractant will slowly disperse into the water when submersed in water within a temperature range of 45-85° F. over a period of 15 to 30 minutes or approximately 20-24 casts.

In use, the fish attractant is applied to a lure or a fish hook and the lure or hook is cast into a body of water containing fish. The attractant containing scent permeates into the water surrounding the lure or hook to attract the fish. The fish attractant will slowly disperse into the water when submersed in water within a temperature range of 45-85° F. over a period of 15 to 30 minutes or approximately 20-24 casts. The resulting fish attractant reflects UV light which is the primary light under water and results in an increased visibility of any coated lure to fish.

The fish attractant according to the invention is desirably formulated by first introducing the component having the lowest melting point into a reaction/mixing vessel and heating to slowly melt the first component. The remaining components are then added under mixing preferably in order by the next lowest melting point until the highest melting point has been added. According to the invention, the temperature is raised slowly while on low heat under continuous stirring. A preferred composition of the invention is formulated as follows:

The first component, polyethylene glycol, is charged into a heated mixing vessel. The polyethylene glycol has a molecular weight of about 600 mw and represent 16% of the total formula. Polyethylene glycol can solidify at room temperature, thus existing in a non-flowable state and/or in liquid form. This compound has a melting point of approximately 80° F. when it turns into a liquid and is noticeably clear. It is heated until it liquifies. The second component petrolatum preferably petroleum jelly is added to the mixing vessel in the amount of 14% having a melting point of 99° F. plus or minus 5° F. It is added in lump amounts being of that it exists in high viscosity form and is non-flowable in its natural state. It is mixed and stirred into the first component and upon reaching a temperature of 100° F.-105° F. becomes a fluid and combines into a flowing liquid consistency, allowing the two compositions to be mixed thoroughly.

The third component, polyethylene glycol, having a molecular weight of about 1450 mw is added in the amount of 25% of total weight, having a melting point of 115° F., plus or minus 5° F. to the heated vessel under mixing. The natural state of this substance is granular and so is poured into the heated vessel slowly allowing the first pours to begin to melt before more is added. At 120° F. plus or minus 5° F. all three of the components are melted to liquid form and the contents are maintained by constant, slow stirring.

The fourth component, polyethylene wax, comprising 15% of the total weight of the composition, with a molecular weight of approximately 400 mw, plus or minus 10% is next added. This material requires at 165°-170° F. temperature to melt down to liquid form and to be combined into the liquid formulation. To achieve a homogenous mixture, stirring is desirable to keep temperature consistent throughout the heating vessel.

Once the mixture reaches 165°-175° F. and the mixture appears to be thoroughly combined by visual inspection, the fifth component, the scent, is added to the extent of about 30% of the total weight and stirred without any temperature boost. Preferably, the scent is preheated to 140° F. so to not drop the mixture temperature when added. In less than 5 minutes at low heat, monitoring a consistent 165°-175° F. the scent is combined into the mixture. The mixture is maintained at heat, monitored with an alarm thermometer and ready to pour into a container and allowed to cool in room temperature for 60 minutes. The mixture is not allowed to boil. The scents used are processed from real bait and preferably distilled into high viscosity gel form, and bacteria is stabilized for prolonged shelf life. The scents range from nightcrawler, crawfish, threadfin shad, gizzard shad, minnow, shiner, rainbow trout, leech, menhaden, mullet, crab, shrimp, tuna, krill, sardine and more. The scents used in formulation are proteins produced from real animals.

EXAMPLES

Fishing for Northern Pike in late September mid-afternoon in a calm river in 8 to 12 feet of water.

The conditions were stained waters, long weed edges, a sandy bottom with a water temp of low 60° 'sF.

Two fishermen used a fish attractant as described herein, one did not. The scent used was the Muskie/Pike formula, made from Gizzard Shad, minnows grubs and shiners, used in 30% of formula. The wax based portion was formulated as follows: PEG 600 was used in 16%, PEG 1450 was used in 25%, PE 400 was used in 15% and petrolatum was added to 14%.

One fisherman coated a spinner bait on the blades and on the ribbed rubber trailer and pulled in a 10 lb pike.

In addition the same fisherman caught three more 2 lb. pikes within one hour.

The second fisherman caught a 5 lb 2 oz and a 3 lb 10 oz in the same hour trolling along the weed bed edge using a ⅜ oz jig and rubber trailer coated with the same scent.

The one fisherman that did not use the composition did not land any pike, but did hook a big one that spit the hook near the boat.

On another lake in late May, fishing for Crappies and Largemouth Bass in 10 to 14 feet of water, sandy bottom in water temperature of high 50°'s F.

Water was stained and cloudy and so the bait of choice were white 1½" rubber tadpoles and a white ¹⁄₁₆ oz. jig head.

Two fishermen, using the same set up, fishing alongside one another, same side of boat.

One used the fish attractant described with Monster Bass scent on the rubber tadpole and one used no attractant at all. The fish attractant was the same as described above in the first example, except reducing the PEG 1450 by 3% and adding pure granular sugar to an amount of 3%, to increase dispersion while maintaining the 30% scent additive amount.

The one using the bass scent, comprised of nightcrawler, crawfish, shad and minnow caught only Largemouth Bass, two 2½ lb'ers and one 3 lb'er, within 45 minutes.

The one fishing without the fish attractant pulled in only Crappies, Blacks and Whites, 1½ to 2 lbs and caught no bass at all.

Fishing on the Columbia River in Oregon in November, two fishermen fished on opposite sides of a boat with 2 oz gold finished spoons for Steelheads, one port side, one starboard.

Trolling in low 50°'s F at low speed, one used the composition described above, one did not. The scent used was 'Sweet Shrimp'. The formula consisted of 15% PEG 600, 22% PEG 1450, 14% PE 400, 14% petrolatum, 5% sea salt and 30% sweet shrimp scent.

The one using the fish attractant according to the invention coated spoons caught 2× the number of Steelhead vs. the one that did not use the fish attractant over a morning of fishing.

Two fishermen fishing with the same set-up using a 9" purple rubber worm with a curly tail, a 3/0 offset worm hook and a ½ oz bullet weight. One fisherman applied the fish attractant according having night crawler scent, the other did not and used no added scent.

The formula applied was 16% PEG 600, 24% PEG 1450, 15% PE 400, 4%, salt, petrolatum 12% and scent added was at 29%.

Over the course of an hour and a half while fishing in rocky bottom water of 10-12' depth, the fisherman using the attractant according to the invention caught four largemouth bass ranging between 2½ and 3% lbs, while the other fisherman caught no fish, had one nibble but was not able to set the hook.

One aspect of the fish attractant is that not only does it disperse in water but also offers an acceptable taste ensuring the fish will hold onto the lure for a longer time giving the fisherman more chance to set a hook and catch the fish.

The foregoing is considered as illustrative only to the principles of the invention. Further, since numerous changes and modification will occur to those skilled in the art, it is not desired to limit the invention to the exact construction and operation shown and described above, and accordingly, all suitable modifications and equivalents may be resorted to, falling within the scope of the invention.

The invention claimed is:

1. A fish attractant comprising:
   a) one or more polyethylene glycol polymers having a mw of about 300 to 4600 in an amount of 19% to 53% by weight of said fish attractant;
   b) a polyethylene wax having a mw of about 220 to 560 in an amount of about 7% to 22% by weight of said fish attractant;
   c) petroleum jelly in an amount of about 8% about 24% by weight of said fish attractant;
   d) a scent in an amount sufficient to attract fish when immersed in water.

2. A fish attractant comprising:
   a) a polyethylene glycol polymer having a mw of about 300 to 960 in an amount of 9% to 22% by weight of said fish attractant;
   b) a polyethylene glycol polymer having a mw of 1200 to 3600 in an amount of 18% to 31% by weight of said fish attractant;
   c) a polyethylene wax having a mw of about 220 to 560 in an amount of about 5% to 23% by weight of said fish attractant;
   d) petroleum jelly in an amount of about 9% to 22% by weight of said fish attractant;
   e) a scent in an amount sufficient to attract fish when immersed in water.

3. The fish attractant according to claim 1 wherein said scent is in an amount of about 15% to 60% by weight of said fish attractant.

4. The fish attractant according to claim 2 wherein said scent is in an amount of about 15% to 60% by weight of said fish attractant.

5. A fish attractant comprising:
   a) a polyethylene glycol polymer having a mw of 540 to 660 in an amount of 13% to 19% by weight of said fish attractant;
   b) a polyethylene glycol polymer having a mw of 1150 to 1750 in an amount of 19% to 32% by weight of said fish attractant;
   c) a polyethylene wax having a mw of about 220 to 560 in an amount of about 12% to 18% by weight of said fish attractant;
   d) petroleum jelly in an amount of about 10% to 18% by weight of said fish attractant;
   e) a scent in an amount of about 20% to 46% by weight of said fish attractant.

6. The fish attractant according to claim 5 wherein said scent is derived from a natural bait typically consumed by fish in the wild.

7. The fish attractant according to claim 5 wherein said scent is derived from fish.

8. The fish attractant according to claim 2 further comprising coating a lure with said attractant to provide UV reflective lure.

9. The fish attractant according to claim 5 further comprising coating a lure with said attractant to provide UV reflective lure.

10. The fish attractant according to claim 5 further comprising 3% to 6% salt or sugar or a mixture of salt and sugar.

11. The fish attractant according to claim 5 further comprising 3% to 6% salt.

12. The fish attractant according to claim 5 further comprising 3% to 6% sugar.

13. The fish attractant according to claim 5 further comprising 3% to 6% of a mixture of salt and sugar.

14. A method of preparing a fish attractant comprising:
mixing a polyethylene glycol polymer having a mw of 540 to 660 in an amount of 13% to 19% by weight of said fish attractant with a polyethylene glycol polymer having a mw of 1200 to 1700 in an amount of 20% to 30% by weight of said fish attractant at a temperature of 110° F. to 125° F. to form a flowable mixture;
adding a polyethylene wax having a mw of about 320 to 480 in an amount of about 12% to 18% by weight of said fish attractant to said mixture under agitation at a temperature of 165° F. to 175° F. to form a flowable mixture;
adding petroleum jelly in an amount of about 9% to 18% by weight of said fish attractant at a temperature of 140° F. to 175° F. to form a flowable mixture;
adding a scent in an amount of about 20% to 44% by weight of said fish attractant said mixture remaining flowable;
filling a container with said mixture and cooling said container to room temperature to form creamy, sticky substance than can be easily applied to a fishing lure.

15. The method of claim 14 wherein said formed substance reflects UV light under water.

16. A fishing lure comprising;
coating said fishing lure with a fishing attractant comprising
a) a polyethylene glycol polymer having a mw of about 300 to 960 in an amount of 10% to 22% by weight of said fish attractant;
b) a polyethylene glycol polymer having a mw of 1200 to 3600 in an amount of 14% to 36% by weight of said fish attractant;
c) a polyethylene wax having a mw of about 220 to 560 in an amount of about 11% to 19% by weight of said fish attractant;
d) petroleum jelly in an amount of about 10% to 23% by weight of said fish attractant;
e) a scent in an amount sufficient to attract fish when immersed in water;
f) said lure being UV reflective under water.

* * * * *